(12) United States Patent
Goto

(10) Patent No.: US 11,437,123 B2
(45) Date of Patent: Sep. 6, 2022

(54) BIOLOGICAL INFORMATION PROCESSING APPARATUS AND BIOLOGICAL INFORMATION PROCESSING SYSTEM

(71) Applicant: Kazuma Goto, Ishikawa (JP)

(72) Inventor: Kazuma Goto, Ishikawa (JP)

(73) Assignee: Ricoh Company, Ltd., Tokyo (JP)

( * ) Notice: Subject to any disclaimer, the term of this patent is extended or adjusted under 35 U.S.C. 154(b) by 608 days.

(21) Appl. No.: 16/281,228

(22) Filed: Feb. 21, 2019

(65) Prior Publication Data

US 2019/0287653 A1 Sep. 19, 2019

(30) Foreign Application Priority Data

Mar. 19, 2018 (JP) .............................. JP2018-051525

(51) Int. Cl.
| | |
|---|---|
| *G01N 33/48* | (2006.01) |
| *G01N 33/50* | (2006.01) |
| *G16B 40/10* | (2019.01) |
| *G16B 50/20* | (2019.01) |
| *G06F 17/18* | (2006.01) |

(52) U.S. Cl.
CPC .............. *G16B 40/10* (2019.02); *G06F 17/18* (2013.01); *G16B 50/20* (2019.02)

(58) Field of Classification Search
CPC ......... G16B 40/10; G16B 50/20; G06F 17/18; A61B 5/7203; A61B 5/7264; G16H 40/60
See application file for complete search history.

(56) References Cited

U.S. PATENT DOCUMENTS

| 5,774,497 A * | 6/1998 | Block ................. H04N 17/004 348/464 |
| 2015/0119745 A1* | 4/2015 | Similowski ......... A61M 16/026 600/544 |

FOREIGN PATENT DOCUMENTS

| JP | 10-080409 | 3/1998 |
| JP | 2017-093760 A | 6/2017 |
| JP | 2017-148404 | 8/2017 |
| WO | WO-2017/085062 A1 | 5/2017 |
| WO | WO-2017/120388 A1 | 7/2017 |
| WO | WO2017/150207 A1 | 9/2017 |

OTHER PUBLICATIONS

English machine translation of WO2017/150207 A1. (Year: 2021).*

(Continued)

*Primary Examiner* — Russell S Negin
(74) *Attorney, Agent, or Firm* — Harness, Dickey & Pierce P.L.C.

(57) ABSTRACT

A biological information processing apparatus and a biological information processing system. The biological information processing apparatus includes a setter configured to obtain a plurality of pieces of biological information and to set a reference used for discrimination of the plurality of pieces of biological information based on a feature amount calculated for each of the pieces of biological information, and a calculator configured to perform addition average of, among the obtained plurality of pieces of biological information, pieces of biological information that have been discriminated based on the reference. The biological information processing system includes a biological information detecting apparatus and the biological information processing apparatus.

8 Claims, 13 Drawing Sheets

(56) References Cited

OTHER PUBLICATIONS

English machine translation of JP10-80409. (Year: 2021).*
English machine translation of JP2017-148404. (Year: 2021).*
CA Office Action dated Nov. 30, 2021 in Japanese patent application No. 2018-051525.

* cited by examiner

FIG. 4
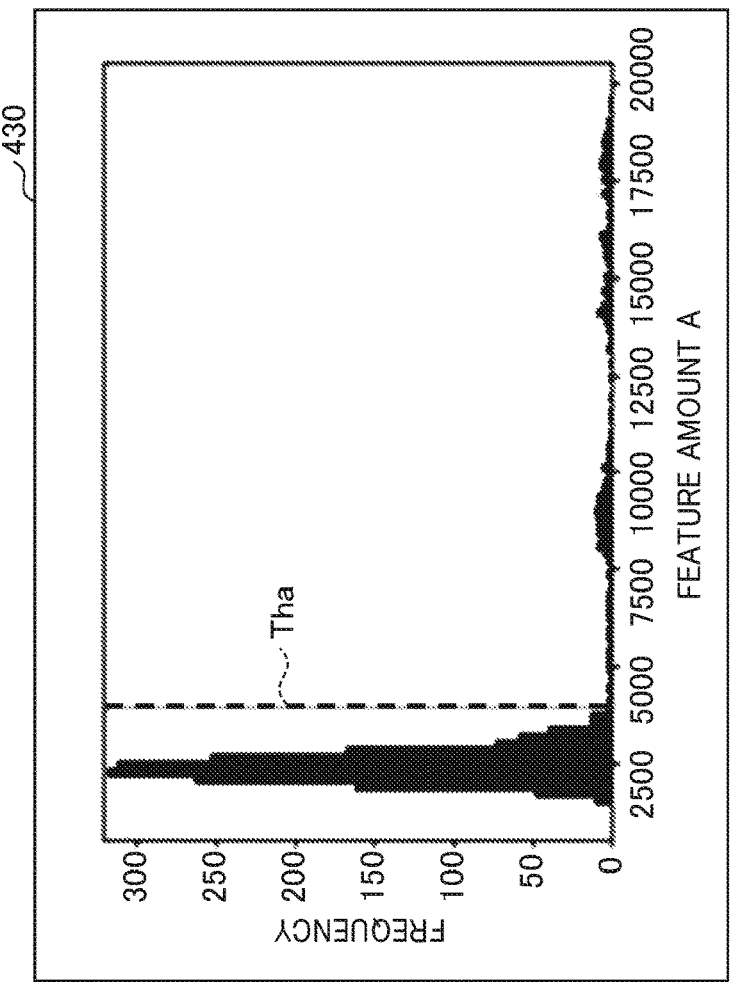
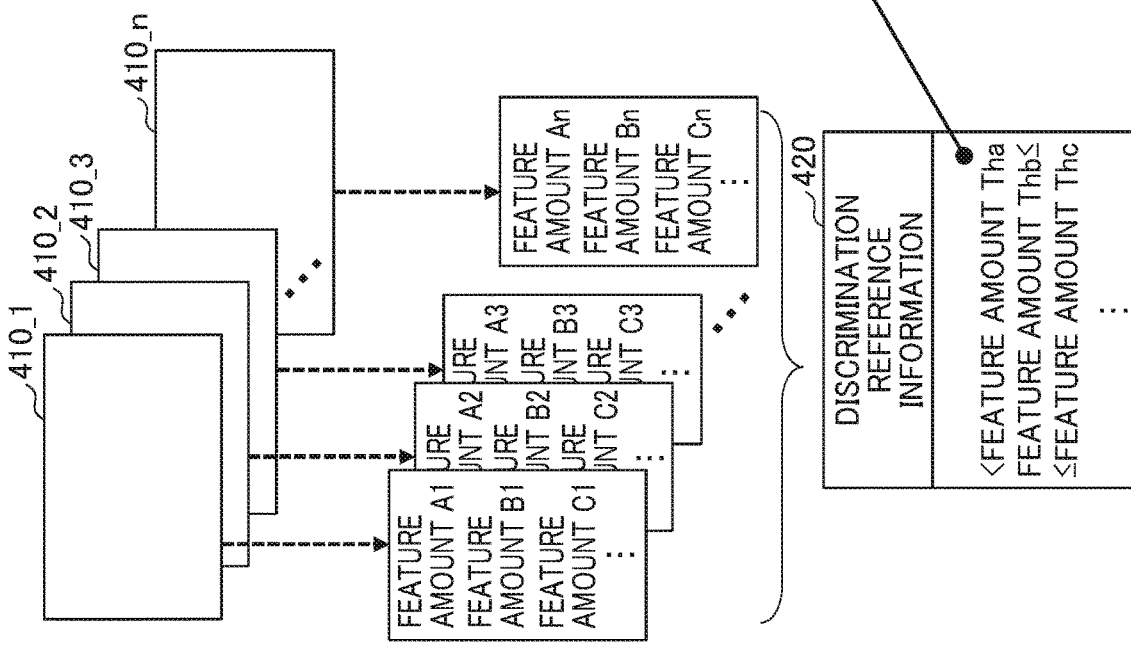

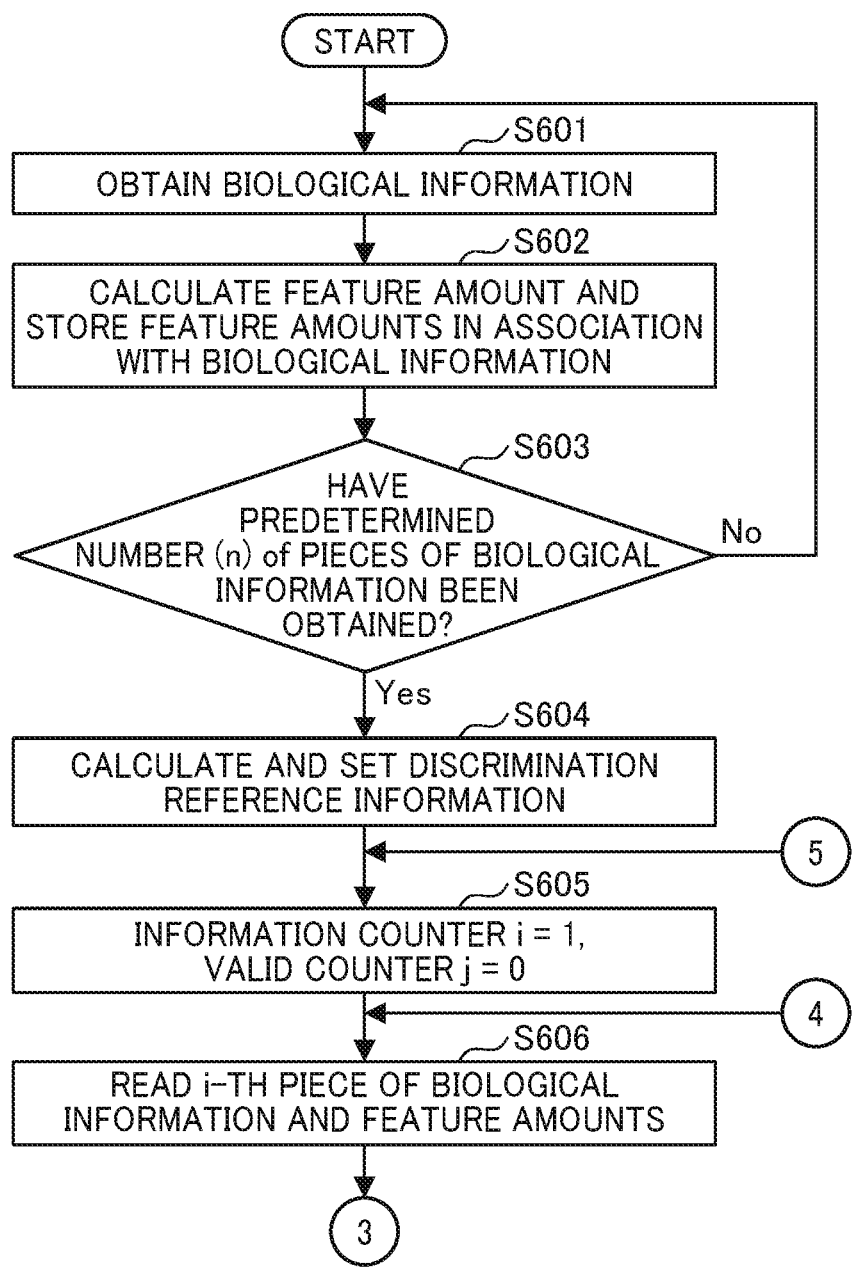

BIOLOGICAL INFORMATION PROCESSING APPARATUS AND BIOLOGICAL INFORMATION PROCESSING SYSTEM

CROSS-REFERENCE TO RELATED APPLICATIONS

This patent application is based on and claims priority pursuant to 35 U.S.C. § 119(a) to Japanese Patent Application No. 2018-051525, filed on Mar. 19, 2018, in the Japan Patent Office, the entire disclosure of which is hereby incorporated by reference herein.

BACKGROUND

Technical Field

The present disclosure relates to a biological information processing apparatus and a biological information processing system.

Description of the Related Art

As known in the art, signals from living bodies (biosignals) are weak and are easily affected by electric or magnetic noise at the time of detection. In order to deal with such a situation, for example, a method for enhancing biological information by using addition average is proposed in the art.

SUMMARY

Embodiments of the present disclosure described herein provide a biological information processing apparatus and a biological information processing system. The biological information processing apparatus includes a setter configured to obtain a plurality of pieces of biological information and to set a reference used for discrimination of the plurality of pieces of biological information based on a feature amount calculated for each of the pieces of biological information, and a calculator configured to perform addition average of, among the obtained plurality of pieces of biological information, pieces of biological information that have been discriminated based on the reference. The biological information processing system includes a biological information detecting apparatus and the biological information processing apparatus.

BRIEF DESCRIPTION OF THE SEVERAL VIEWS OF THE DRAWINGS

A more complete appreciation of the disclosure and many of the attendant advantages and features thereof can be readily obtained and understood from the following detailed description with reference to the accompanying drawings, wherein:

FIG. 4 is a diagram illustrating the flow of a process for calculating discrimination reference information used for discrimination of a plurality of pieces of biological information, according to an embodiment of the present disclosure;

FIG. 9A and FIG. 9B are a second flowchart illustrating flow of biological information processing performed by a biological information processing apparatus, according to an embodiment of the present disclosure.

Figure 1:
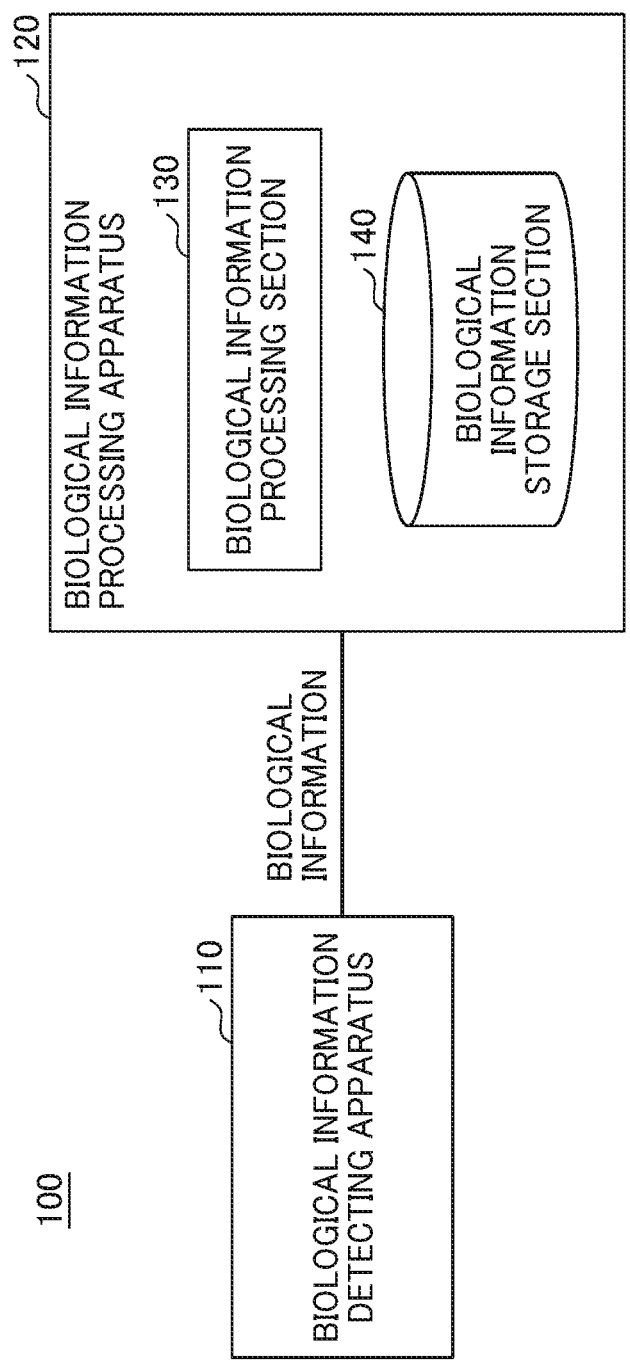
FIG. 1 is a diagram illustrating a system configuration of a biological information processing system according to an embodiment of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Now, the embodiments will be described below in detail. Note that components having substantially the same function and configuration are denoted by the same reference numeral in the specification and drawings related to the embodiments so that a repeated description can be omitted.

First Embodiment

System Configuration of Biological Information Processing System

First of all, a system configuration of a biological information processing system according to a first embodiment will be described.

FIG. 1 is a diagram illustrating the system configuration of a biological information processing system 100 according to the present embodiment.

As illustrated in FIG. 1, a biological information processing system 100 includes a biological information detecting apparatus 110 and a biological information processing apparatus 120. The biological information detecting apparatus 110 and the biological information processing apparatus 120 are connected to each other so that communication can be performed therebetween.

The biological information detecting apparatus 110 detects biological information of an examinee as time-series signal data and transmits the detected biological information to the biological information processing apparatus 120. Examples of the biological information detecting apparatus 110 include any apparatus that detects biological information of the examinee, such as an evoked potential measuring apparatus, an electroencephalograph, or a biomagnetism measuring apparatus.

A biological information processing program is installed in the biological information processing apparatus 120, and the program is executed so that the biological information processing apparatus 120 serves as a biological information processing section 130.

The biological information processing section 130 is an example of a setter. The biological information processing section 130 obtains a plurality of pieces of biological information transmitted from the biological information detecting apparatus 110, and stores the obtained plurality of pieces of biological information in a biological information storage section 140. In addition, the biological information processing apparatus 120 calculates "discrimination reference information" used for discrimination of the obtained plurality of pieces of biological information, and sets the calculated discrimination reference information.

The biological information processing section 130 is also an example of a calculator. On the basis of the set discrimination reference information, the biological information processing section 130 discriminates the obtained plurality of pieces of biological information. In addition, by using the discriminated biological information, the biological information processing section 130 performs "addition average processing." The result of the addition average processing is stored in the biological information storage section 140 as a biological information processing result.

Hardware Configuration of Biological Information Processing Apparatus

Next, a hardware configuration of the biological information processing apparatus 120 will be described.

Figure 2:
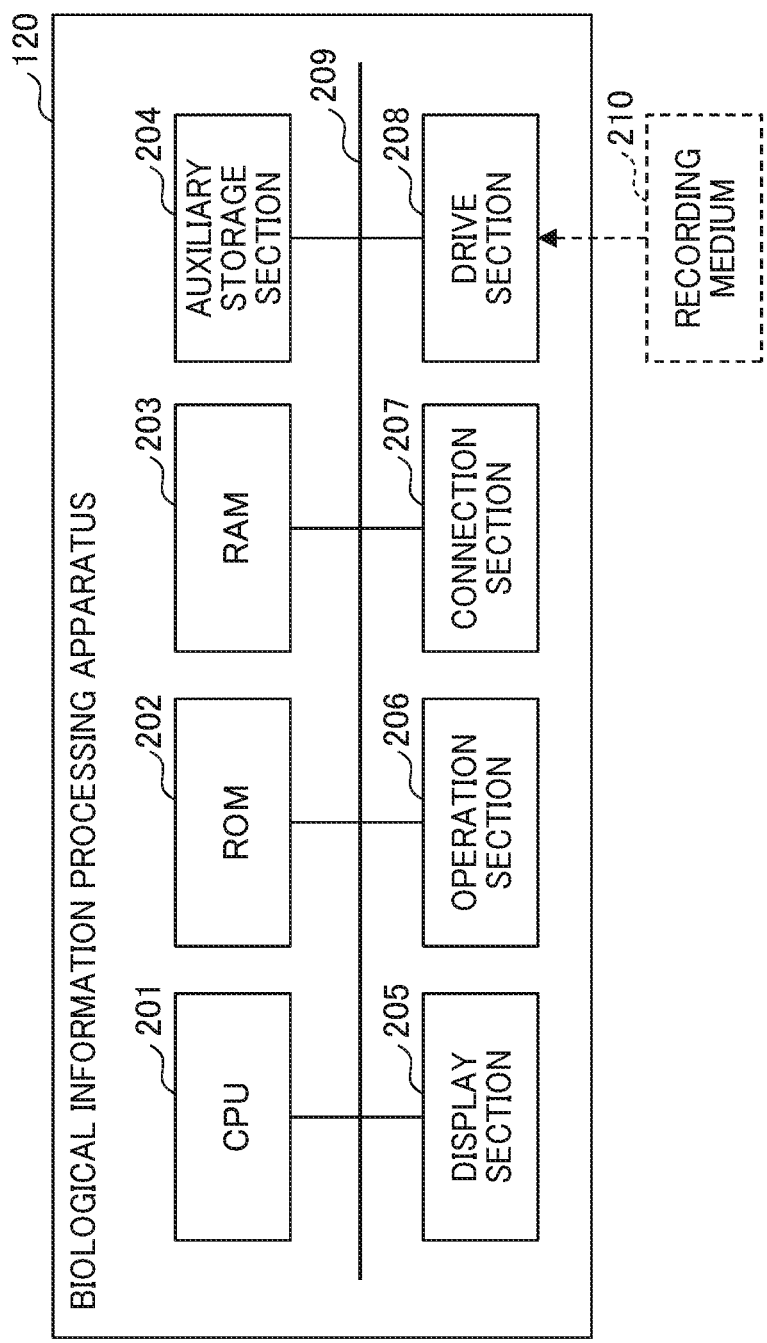
FIG. 2 is a diagram illustrating a hardware configuration of a biological information processing apparatus according to an embodiment of the present disclosure.

FIG. 2 is a diagram illustrating the hardware configuration of the biological information processing apparatus 120 according to the present embodiment.

As illustrated in FIG. 2, the biological information processing apparatus 120 includes a central processing unit (CPU) 201, a read-only memory (ROM) 202, and a random access memory (RAM) 203. The CPU 201, the ROM 202, and the RAM 203 form a so-called computer.

In addition, the biological information processing apparatus 120 also includes an auxiliary storage section 204, a display section 205, an operation section 206, a connection section 207, and a drive section 208. Note that the hardware components of the biological information processing apparatus 120 are connected to each other via a bus 209.

The CPU 201 is an arithmetic device that executes programs (e.g., biological information processing program) installed in the auxiliary storage section 204.

The ROM 202 is a non-volatile memory. The ROM 202 serves as a main storage device that stores programs, data, and the like that are used by the CPU 201 to execute the programs installed in the auxiliary storage section 204. Specifically, the ROM 202 serves as a main storage device that stores, for example, a boot program for basic input/output system (BIOS) or extensible firmware interface (EFI).

The RAM 203 is a volatile memory such as a dynamic random access memory (DRAM) or a static random access memory (SRAM). The RAM 203 serves as a main storage device that provides a work area in which the programs installed in the auxiliary storage section 204 are loaded when the CPU 201 executes the programs.

The auxiliary storage section 204 is an auxiliary storage device that stores programs or information used when the programs are executed. For example, the biological information storage section 140 is realized in the auxiliary storage section 204.

The display section 205 is a display device that displays, for example, an internal state of the biological information processing apparatus 120. The operation section 206 is an input device used when instructions are input to the biological information processing apparatus 120. The connection section 207 is a connection device for connecting the biological information detecting apparatus 110 and the biological information processing apparatus 120 to each other so that communication can be performed therebetween.

The drive section 208 is a device in which a recording medium 210 is set. The recording medium 210 herein includes a medium that optically, electrically, or magnetically records information, such as a compact-disk read-only memory (CD-ROM), a flexible disk, or a magneto-optical disk. In addition, the recording medium 210 may also include, for example, a semiconductor memory that electrically records information, such as a ROM or a flash memory.

Note that the programs to be installed in the auxiliary storage section 204 are installed in the following manner. For example, the recording medium 210 that has been distributed is set in the drive section 208, and the programs recorded in the recording medium 210 are read by the drive section 208. Alternatively, the programs to be installed in the auxiliary storage section 204 may be installed by being downloaded from a network through the connection section 207.

Examples of Biological Information

Next, the biological information to be transmitted from the biological information detecting apparatus 110 will be described.

Figure 3:
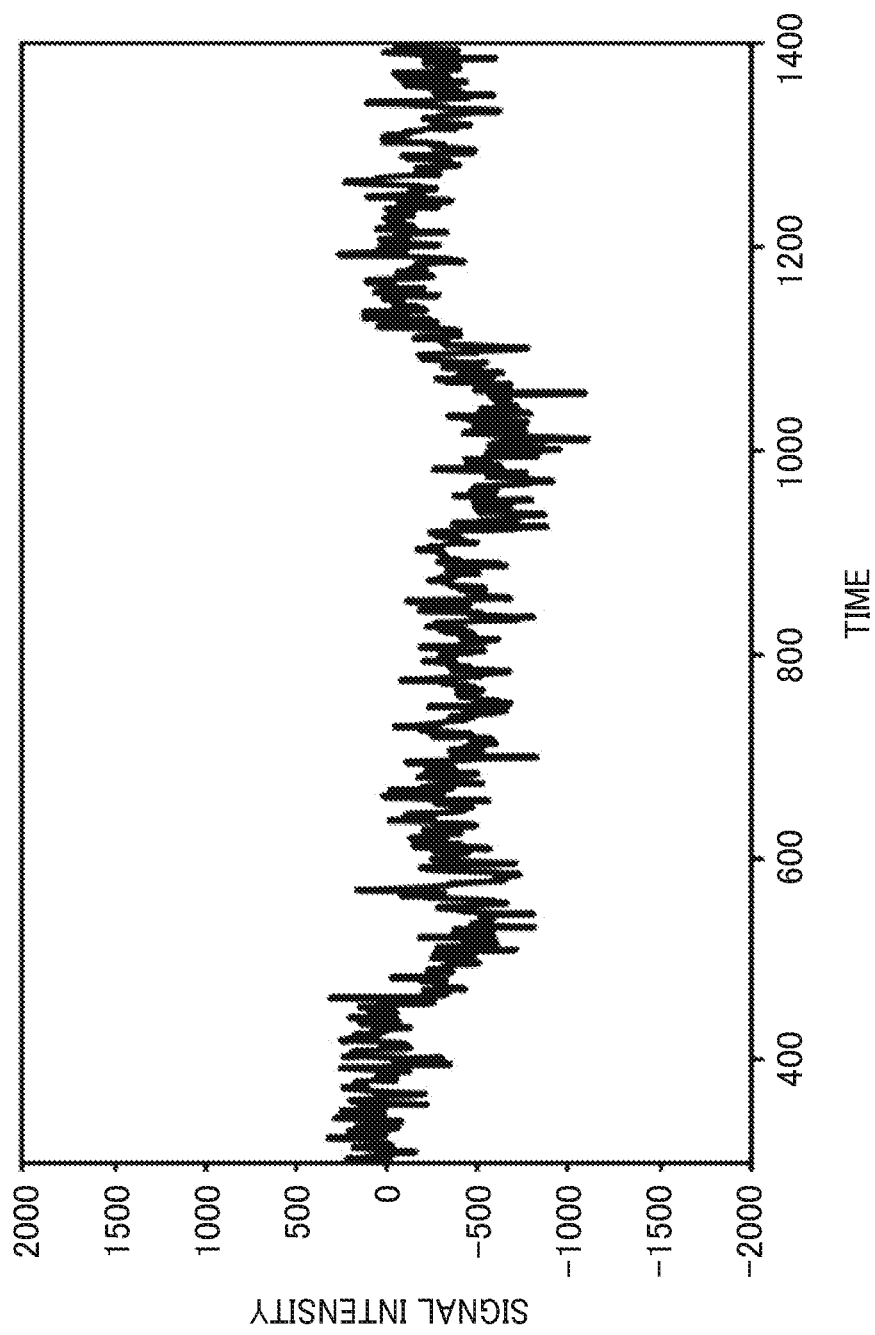
FIG. 3 is a diagram illustrating biological information according to an embodiment of the present disclosure.

FIG. 3 is a diagram illustrating the biological information according to the present embodiment.

In FIG. 3, the horizontal axis represents time, and the vertical axis represents signal intensity. As illustrated in FIG. 3, the biological information to be transmitted from the biological information detecting apparatus 110 is time-series signal data. When the biological information detecting apparatus 110 detects the biological information, the biological information to be transmitted from the biological information detecting apparatus 110 is affected by electric or magnetic noise and contains noise as illustrated in FIG. 3.

Flow of Process for Calculating Discrimination Reference Information

Next, flow of a process in which the biological information processing section 130 calculates the discrimination reference information will be described. The plurality of pieces of biological information are discriminated on the basis of the discrimination reference information.

FIG. 4 is a diagram illustrating the flow of a process for calculating the discrimination reference information used for discrimination of the plurality of pieces of biological information, according to the present embodiment.

As illustrated in FIG. 4, the biological information processing section 130 obtains a plurality of pieces of biological information 410_1 to 410_$n$ transmitted from the biological information detecting apparatus 110.

For each of the obtained plurality of pieces of biological information 410_1 to 410_$n$, the biological information processing section 130 calculates a feature amount A, a feature amount B, a feature amount C, and the like. The feature amounts calculated by the biological information processing section 130 include the average, variances, and the like of the signal intensity.

As illustrated in FIG. 4, the feature amount A=A1, the feature amount B=B1, the feature amount C=C1, and the like are calculated for the biological information 410_1. In addition, the feature amount A=A2, the feature amount B=B2, the feature amount C=C2, and the like are calculated for the biological information 410_2. Furthermore, the feature amount A=A3, the feature amount B=B3, the feature amount C=C3, and the like are calculated for the biological information 410_3. Furthermore, the feature amount A=An, the feature amount B=Bn, the feature amount C=Cn, and the like are calculated for the biological information 410_$n$.

The biological information processing section 130 statistically processes the feature amounts, which have been calculated for the plurality of pieces of biological information, according to the type of feature amount so as to calculate discrimination reference information 420. The statistic processing according to the type of feature amount performed by the biological information processing section 130 includes, for example, a process for calculating the average of the feature amounts, a process for calculating the sum of variances of the feature amounts, a process for calculating ½ of the maximum of the feature amounts, and the like, on the basis of a histogram of the feature amounts.

As illustrated in FIG. 4, the biological information processing section 130 has calculated "Tha" as the discrimination reference information for the feature amount A by using the feature amounts A1 to An. In addition, the biological information processing section 130 has calculated "Thb" as the discrimination reference information for the feature amount B by using the feature amounts B1 to Bn. Furthermore, the biological information processing section 130 has calculated "Thc" as the discrimination reference information for the feature amount C by using the feature amounts C1 to Cn.

Note that, as illustrated in FIG. 4, for calculating the discrimination reference information "Tha" by using the feature amounts A1 to An for the feature amount A, the biological information processing section 130 generates a histogram 430 in which the horizontal axis represents the value of the feature amount A and the vertical axis represents frequency. Then, the biological information processing section 130 calculates the value of the feature amount A, which is a predetermined variance, as "Tha". Thus, the biological information processing section 130 can exclude biological information including particular noise from the pieces of biological information 410_1 to 410_$n$.

Flow of Addition Average Processing

Next, flow of a process in which the biological information processing section 130 discriminates the biological information on the basis of the discrimination reference information 420 that has been calculated, and subjects the discriminated biological information to addition average will be described.

Figure 5:
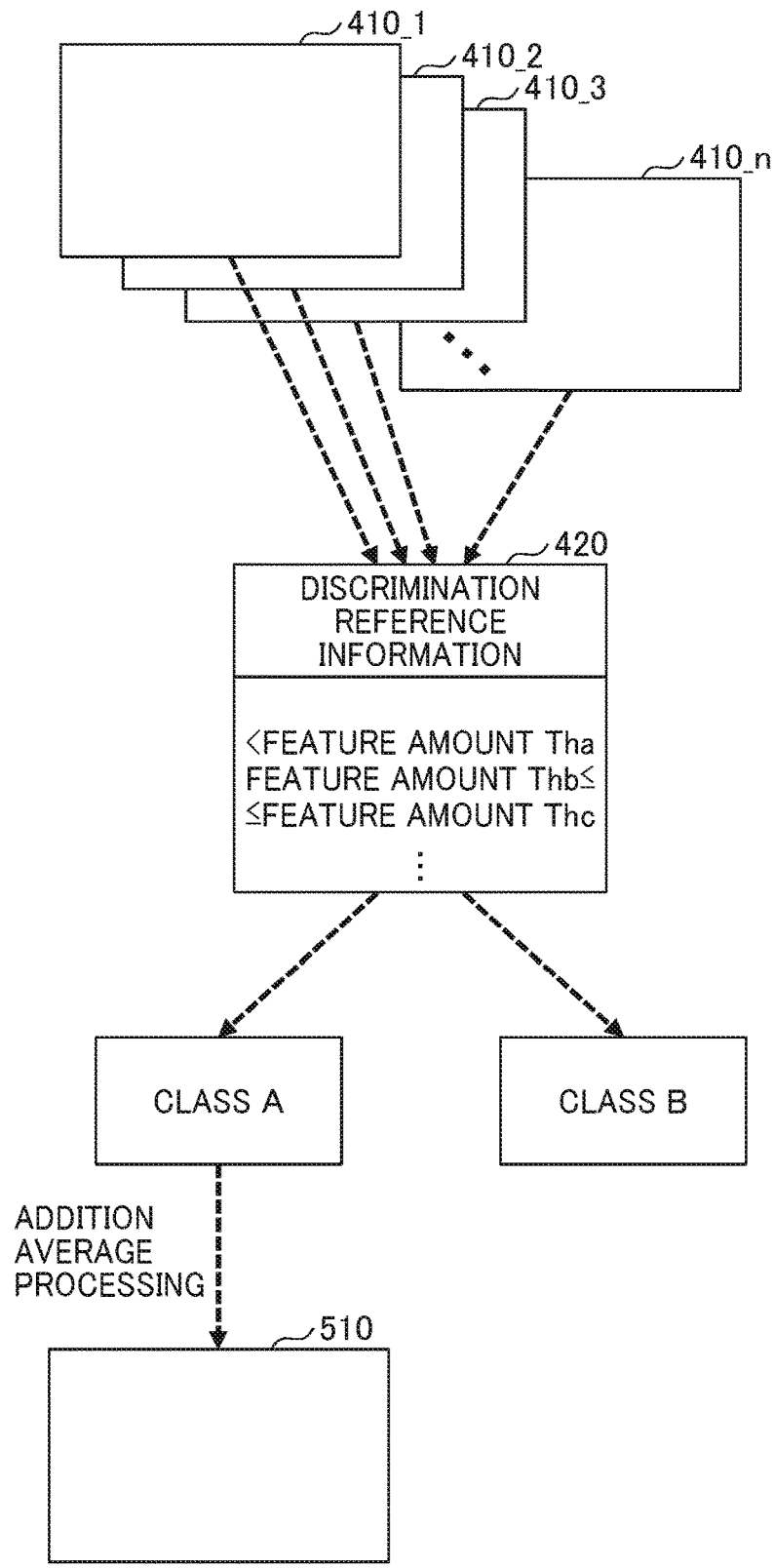
FIG. 5 is a diagram illustrating the flow of addition average processing of biological information discriminated on the basis of the discrimination reference information, according to an embodiment of the present disclosure.

FIG. 5 is a diagram illustrating the flow of addition average processing of the biological information discriminated on the basis of the discrimination reference information 420, according to the present embodiment.

As illustrated in FIG. 5, for each of the obtained plurality of pieces of biological information 410_1 to 410_$n$, the biological information processing section 130 compares the calculated feature amounts with the discrimination reference information 420. The biological information processing section 130 discriminates, as a class A, a piece of the biological information that has been determined to satisfy the discrimination reference information 420 as a result of the comparison with the discrimination reference information 420. On the other hand, the biological information processing section 130 discriminates, as a class B, a piece of the biological information that has been determined to not satisfy the discrimination reference information 420 as a result of the comparison with the discrimination reference information 420.

Furthermore, the biological information processing section 130 performs addition average processing by using pieces of the biological information that have been discriminated as the class A to obtain a biological information processing result 510.

In the above manner, the biological information processing section 130 discriminates the pieces of biological information that are suitable for addition average by using the discrimination reference information 420 to exclude pieces of biological information that contain particular noise, and then the biological information processing section 130 performs addition average processing. Thus, with the biological information processing section 130, influence of noise can be suppressed, and the good biological information processing result 510 can be obtained.

Flow of Biological Information Processing

Next, flow of biological information processing performed by the biological information processing apparatus 120 will be described.

Figure 6A:
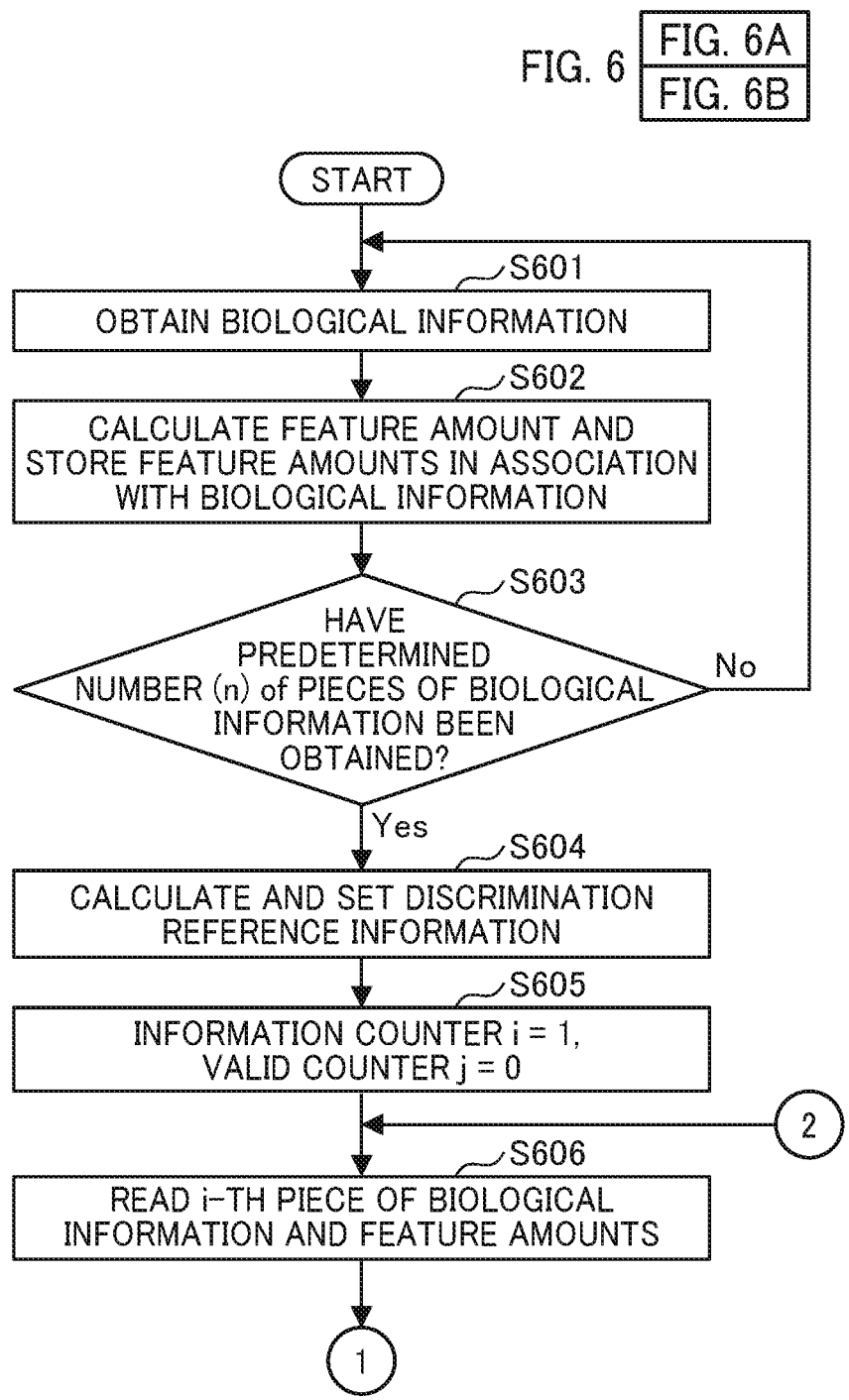
FIG. 6A and FIG. 6B are a first flowchart illustrating flow of biological information processing performed by a biological information processing apparatus, according to an embodiment of the present disclosure.
Figure 6B:
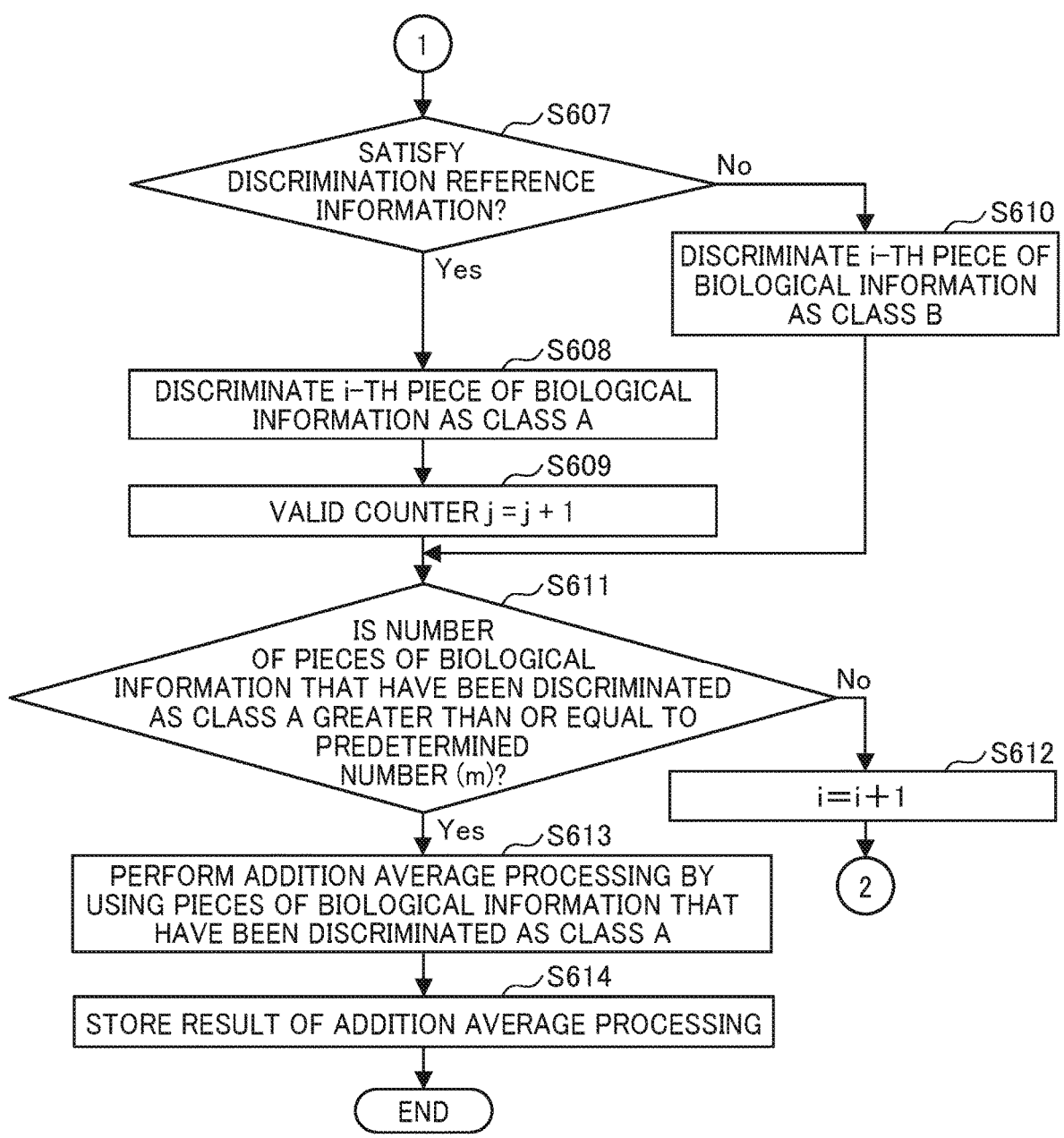

FIG. 6A and FIG. 6B are a first flowchart illustrating the flow of biological information processing performed by the biological information processing apparatus 120, according to the present embodiment.

In step S601, the biological information processing section 130 obtains the plurality of pieces of biological information transmitted from the biological information detecting apparatus 110. In step S602, for each of the obtained plurality of pieces of biological information, the biological information processing section 130 calculates the feature amounts and stores the feature amounts in the biological information storage section 140 in association with the piece of biological information.

In step S603, the biological information processing section 130 determines whether a predetermined number (n) of pieces of biological information 410_1 to 410_$n$ have been obtained from the biological information detecting apparatus 110. If it is determined in step S603 that the predetermined number (n) of pieces of biological information have not been obtained (NO in step S603), the process returns to step S601.

On the other hand, if it is determined in step S603 that the predetermined number (n) of pieces of biological information 410_1 to 410_$n$ have been obtained (YES in step S603), the process proceeds to step S604. In step S604, the biological information processing section 130 statistically processes the feature amounts calculated for each of the predetermined number (n) of pieces of biological information 410_1 to 410_$n$ according to the type of feature amount, thereby calculating and setting the discrimination reference information 420.

In step S605, the biological information processing section 130 substitutes "1" for an information counter i that counts the number of pieces of biological information read from the biological information storage section 140. In addition, the biological information processing section 130 substitutes "0" for a valid counter j that counts the number of pieces of biological information to be used for addition average processing.

In step S606, the biological information processing section 130 reads, from the biological information storage section 140, an i-th piece of biological information and feature amounts that are associated with the i-th piece of biological information.

In step S607, the biological information processing section 130 determines whether the read feature amounts that are associated with the i-th piece of biological information satisfy the discrimination reference information 420. If it is determined in step S607 that the read feature amounts that are associated with the i-th piece of biological information satisfy the discrimination reference information 420, the process proceeds to step S608.

In step S608, the biological information processing section 130 discriminates the i-th piece of biological information as the class A. In step S609, the biological information processing section 130 increments the valid counter j.

On the other hand, if it is determined in step S607 that the read feature amounts that are associated with the i-th piece of biological information do not satisfy the discrimination reference information 420, the process proceeds to step S610. In step S610, the biological information processing section 130 discriminates the i-th piece of biological information as the class B.

In step S611, the biological information processing section 130 determines whether the number (j) of pieces of biological information that have been discriminated as the class A is greater than or equal to a predetermined number (m). If it is determined in step S611 that the number (j) of pieces of biological information that have been discriminated as the class A is less than the predetermined number (m) (NO in step S611), the process proceeds to step S612. In step S612, the biological information processing section 130 increments the information counter i, and then, the process returns to step S606.

On the other hand, if it is determined in step S611 that the number (j) of pieces of biological information that have been discriminated as the class A is greater than or equal to the predetermined number (m) (YES in step S611), the process proceeds to step S613. In step S613, the biological information processing section 130 performs addition average processing by using the pieces of biological information that have been discriminated as the class A.

In step S614, the biological information processing section 130 stores the result of addition average processing in the biological information storage section 140 as the biological information processing result 510.

Specific Example of Biological Information Processing Result

Next, the biological information processing result 510 will be described. The biological information processing result 510 is obtained by the biological information processing section 130 performing addition average processing.

Figure 7:
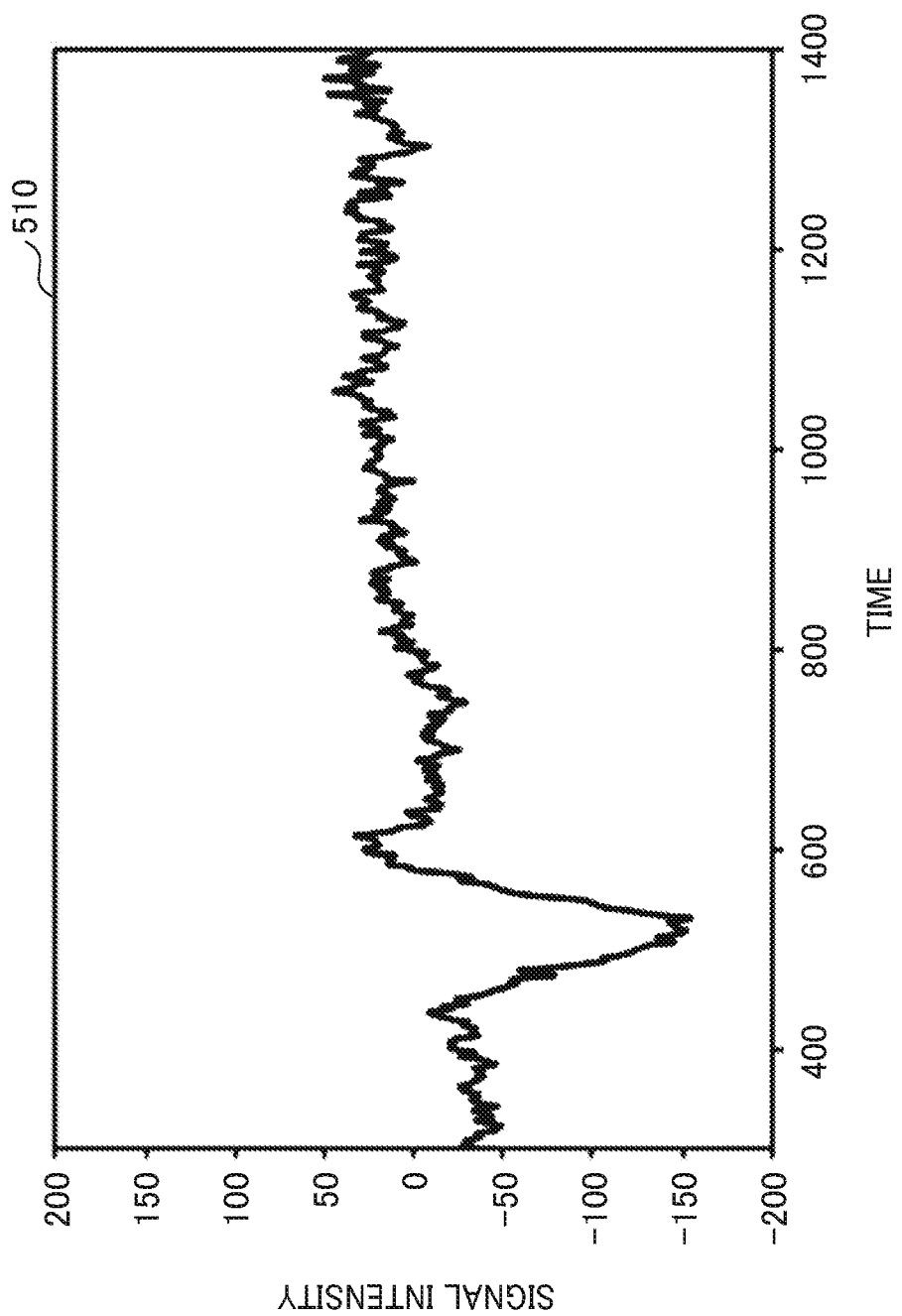
FIG. 7 illustrates a specific example of a biological information processing result, according to an embodiment of the present disclosure.

FIG. 7 is a diagram illustrating a specific example of the biological information processing result 510, according to the present embodiment.

As is clear from the comparison with FIG. 3 (biological information transmitted from the biological information detecting apparatus 110), since the biological information is discriminated on the basis of the discrimination reference information 420, particular noise is canceled. In addition, the addition average processing emphasizes the biological information and also cancels uncorrelated noise. As a result, the good biological information processing result 510 that is less affected by noise can be obtained.

CONCLUSION

As is clear from the above description, the biological information processing system according to the first embodiment obtains a plurality of pieces of biological information, and statistically processes a feature amount that has been calculated for each of the pieces of biological information, so as to calculate discrimination reference information, and discriminates, among the obtained plurality of pieces of biological information, pieces of biological information for which the feature amount satisfies the discrimination reference information, and performs addition average processing by using the discriminated pieces of biological information.

Thus, with the biological information processing system according to the first embodiment, it is possible to discriminate biological information that is suitable for addition average and to exclude biological information that contains particular noise before performing addition average processing. As a result, it is possible to obtain a good biological information processing result that is less affected by noise.

Second Embodiment

In the first embodiment described above, the biological information is discriminated on the basis of the discrimination reference information calculated by statistically processing the feature amounts. In contrast, in a second embodiment, a biological information processing result for biological information that has been discriminated on the basis of the calculated discrimination reference information is displayed so that a user can correct the calculated discrimination reference information. Now, the second embodiment will be described below mainly on differences from the first embodiment.

Flow of Process for Correcting Discrimination Reference Information

First, flow of a process in which the biological information processing section 130 corrects the calculated discrimination reference information 420 will be described.

Figure 8:
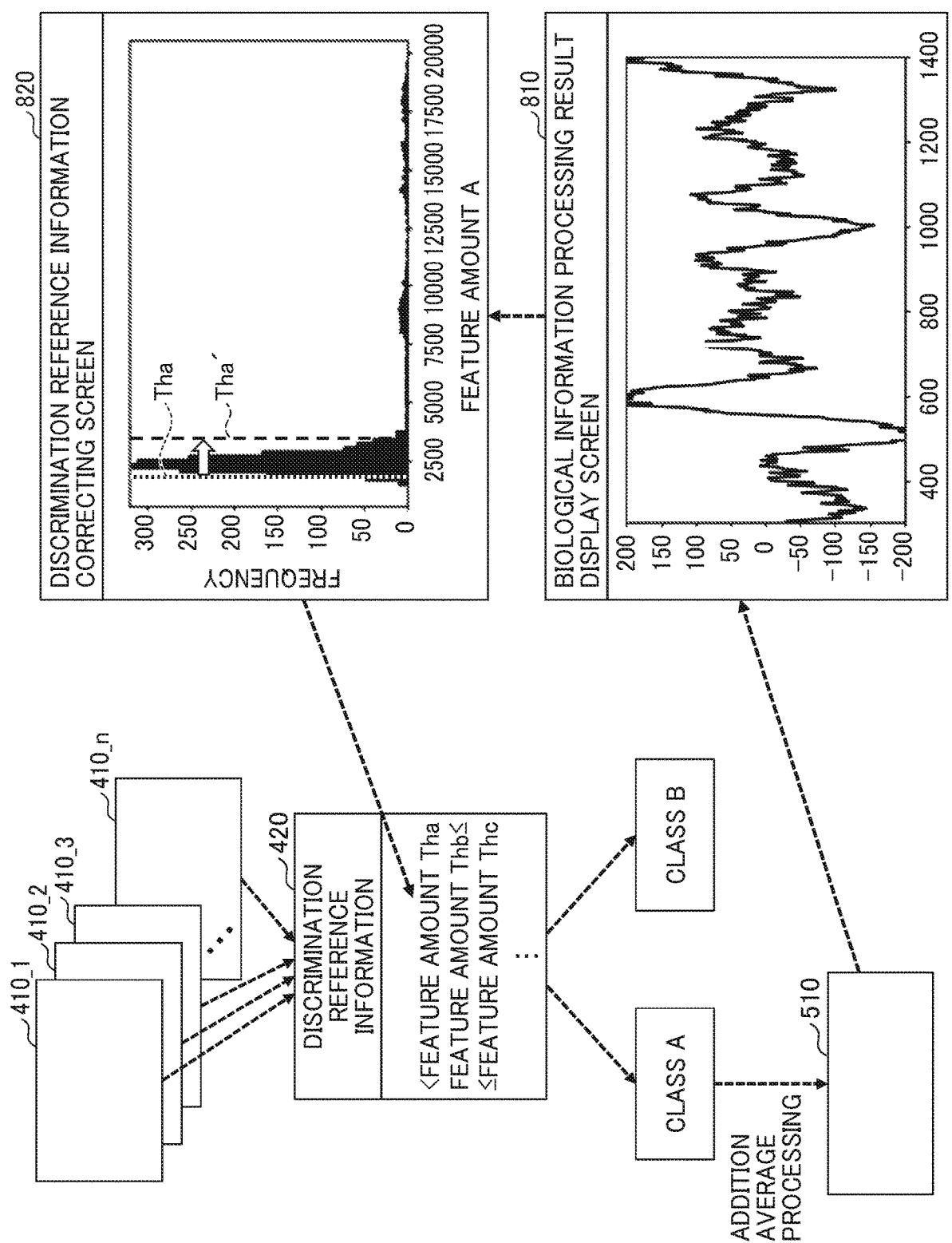
FIG. 8 is a diagram illustrating flow of a process for correcting the discrimination reference information used for discrimination of a plurality of pieces of biological information, according to an embodiment of the present disclosure.

FIG. 8 is a diagram illustrating the flow of a process for correcting the discrimination reference information 420 to be used for discrimination of a plurality of pieces of biological information, according to the present embodiment.

As illustrated in FIG. 8, for each of the obtained plurality of pieces of biological information 410_1 to 410_n, the biological information processing section 130 compares the calculated feature amounts with the discrimination reference information 420. The biological information processing section 130 discriminates, as the class A, a piece of the biological information that has been determined to satisfy the discrimination reference information 420 as a result of the comparison with the discrimination reference information 420. On the other hand, the biological information processing section 130 discriminates, as the class B, a piece of the biological information that has been determined to not satisfy the discrimination reference information 420 as a result of the comparison with the discrimination reference information 420.

Furthermore, the biological information processing section 130 performs addition average processing by using pieces of biological information that have been discriminated as the class A to obtain the biological information processing result 510.

Note that, in the second embodiment, before storing the biological information processing result 510 in the biological information storage section 140, the biological information processing section 130 displays the biological information processing result 510 as a biological information processing result display screen 810 on the display section 205. Thus, a user can judge whether the biological information processing result 510 is a good biological information processing result.

If the user has judged that the biological information processing result 510 is a good biological information processing result, the biological information processing section 130 stores the biological information processing result 510 in the biological information storage section 140.

On the other hand, if the user has judged that the biological information processing result 510 is not a good biological information processing result, the biological information processing section 130 displays a discrimination reference information correcting screen 820 on the display section 205. FIG. 8 illustrates a state in which the histogram generated when the discrimination reference information for the feature amount A is calculated and current discrimination reference information ("Tha") for the feature amount A are displayed.

The biological information processing section 130 displays the discrimination reference information correcting screen 820 on the display section 205 so as to receive a correction instruction of the discrimination reference information from the user. FIG. 8 illustrates a state in which the biological information processing section 130 corrects the discrimination reference information for the feature amount A from "Tha" to "Tha'".

Upon the user's input of the correction instruction of the discrimination reference information on the discrimination reference information correcting screen 820, the biological information processing section 130 sets the corrected discrimination reference information, and discriminates the biological information and performs the addition average processing again. Thus, the biological information processing section 130 can obtain a good biological information processing result.

Flow of Biological Information Processing

Next, flow of biological information processing performed by the biological information processing apparatus 120 will be described.

Figure 9B:
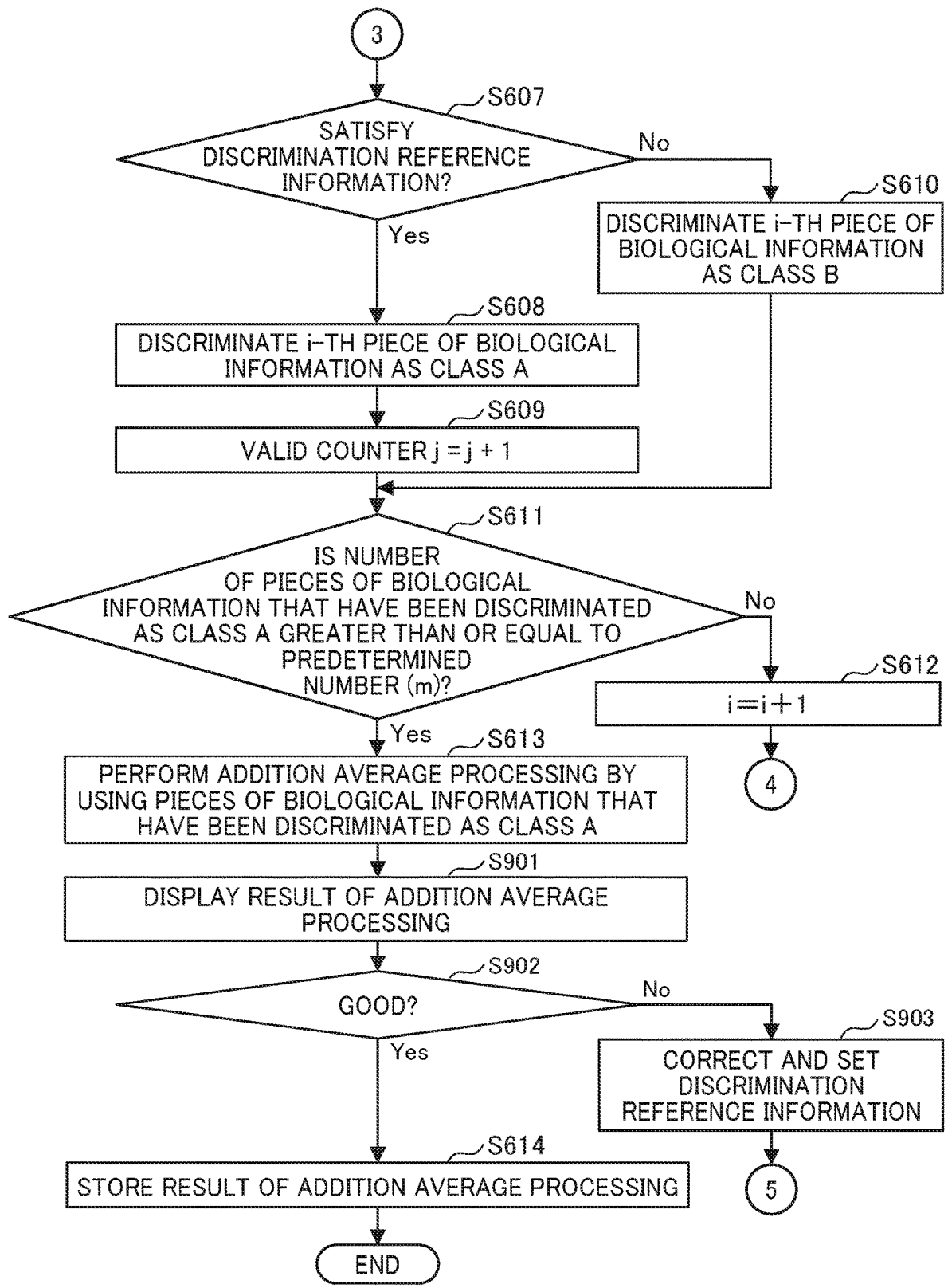

FIG. 9A and FIG. 9B are a second flowchart illustrating the flow of biological information processing performed by the biological information processing apparatus 120, according to the present embodiment.

Differences from the biological information processing described in the first embodiment above with reference to FIG. 6A and FIG. 6B are step S901 to step S903.

In step S901, the biological information processing section 130 displays a result of addition average processing as the biological information processing result display screen 810 on the display section 205. In step S902, the biological information processing section 130 determines whether the user has judged the result of addition average processing as a good biological information processing result.

If it is determined in step S902 that the user has judged the result of addition average processing as a good biological information processing result (YES in step S902), the process proceeds to step S614.

On the other hand, if it is determined in step S902 that the user has judged the result of addition average processing as not a good biological information processing result (NO in step S902), the process proceeds to step S903.

In step S903, the biological information processing section 130 displays the discrimination reference information correcting screen 820 on the display section 205 so as to receive a correction instruction of the discrimination reference information 420. In addition, on the basis of the correction instruction, the biological information processing section 130 corrects the discrimination reference information 420 and sets the corrected discrimination reference information 420, and then the process returns to step S605. Thus, the biological information processing section 130 can perform the process from step S605 to step S902 again.

As is clear from the above description, the biological information processing system according to the second embodiment obtains a plurality of pieces of biological information, and statistically processes a feature amount that has been calculated for each of the pieces of biological information, so as to calculate discrimination reference information, discriminates, among the obtained plurality of pieces of biological information, pieces of biological information for which the feature amount satisfies the discrimination reference information, and performs addition average processing by using the discriminated pieces of biological information, and displays a result of the addition average processing, and if a user has judged the result of the addition average processing as not a good biological information processing result, displays a discrimination reference information correcting screen so as to receive a correction instruction of the discrimination reference information.

Thus, with the biological information processing system according to the second embodiment, even if a good biological information processing result is not obtained at first, it is possible to obtain a good biological information processing result by correcting the discrimination reference information through a simple operation and performing the addition average processing again.

Third Embodiment

In the first and second embodiments described above, the discrimination reference information is calculated, and the obtained plurality of pieces of biological information are discriminated, so that biological information containing particular noise is excluded before the addition average processing is performed. In contrast, in a third embodiment, a function of reducing noise contained in the biological information is further added when the biological information is obtained.

Figure 10A:
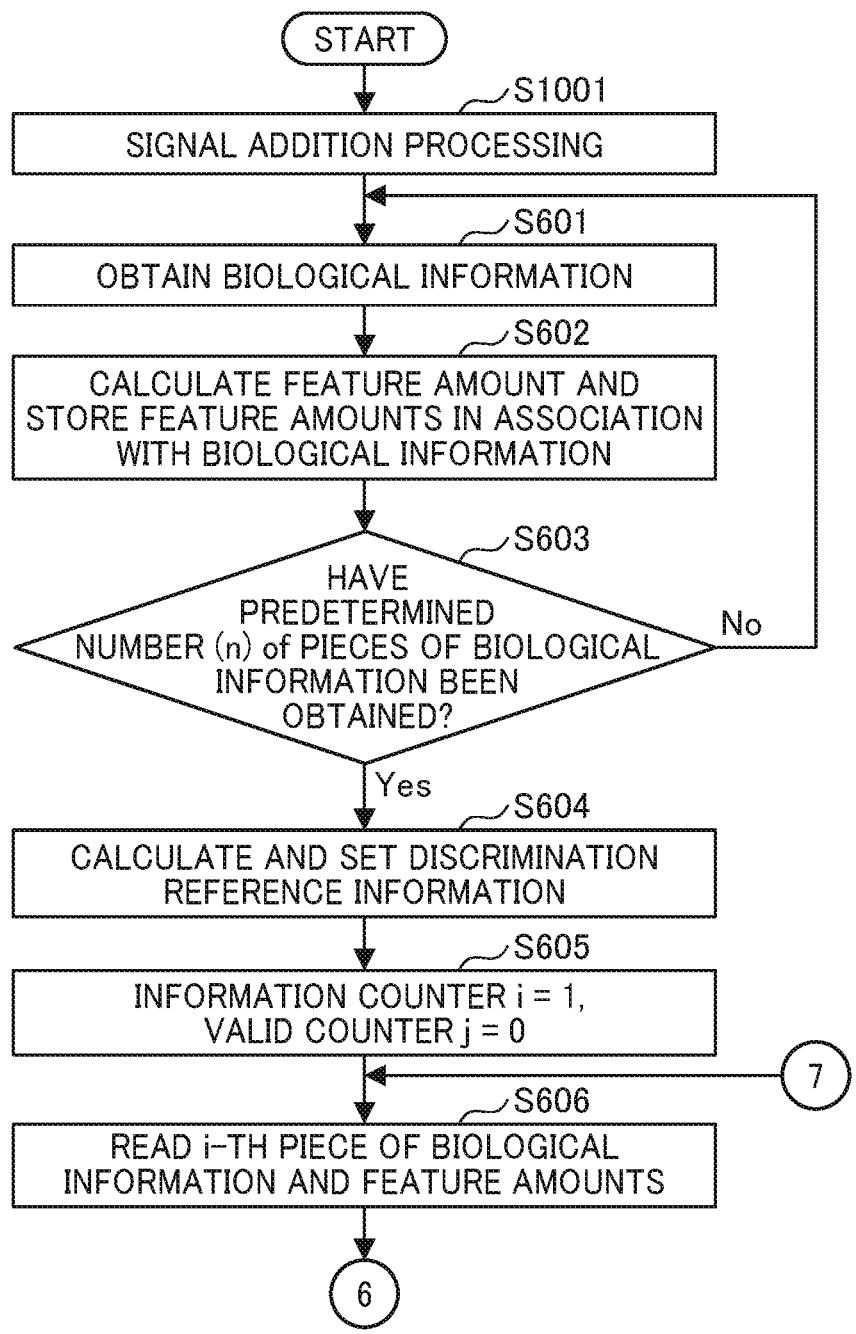
FIG. 10A and FIG. 10B are a third flowchart illustrating flow of biological information processing performed by a biological information processing apparatus, according to an embodiment of the present disclosure.
Figure 10B:
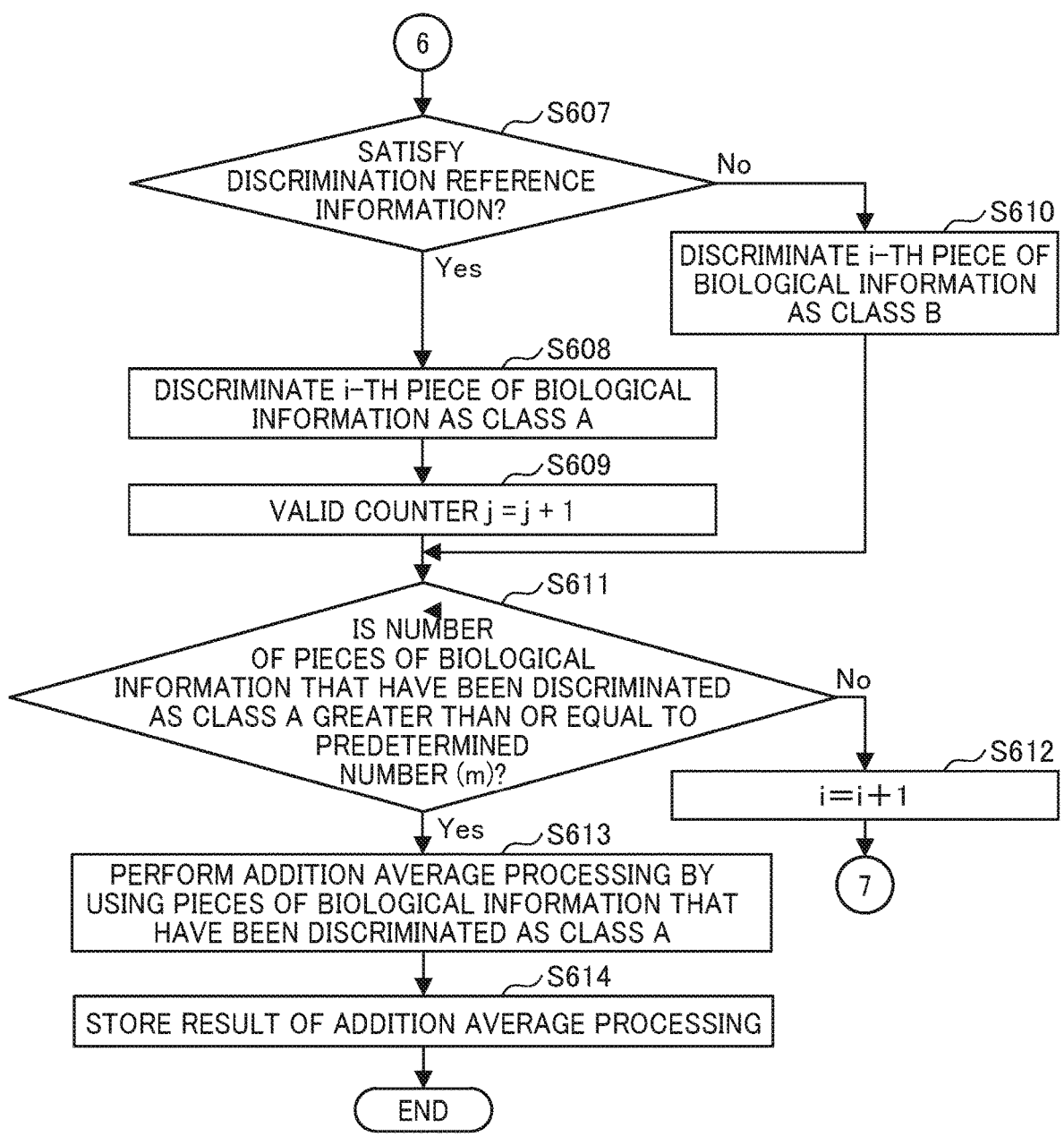

FIG. 10A and FIG. 10B are a third flowchart illustrating flow of biological information processing performed by the biological information processing apparatus 120, according to the present embodiment.

A difference from the biological information processing described in the first embodiment above with reference to FIG. 6A and FIG. 6B is step S1001.

In step S1001, the biological information processing section 130 adds a predetermined signal to the biological information to be transmitted from the biological information detecting apparatus 110 so as to reduce noise. For example, in a case where the biological information detecting apparatus 110 is a biomagnetism measuring apparatus and has measured a magnetism from a living body, the biological information to be transmitted from the biological information detecting apparatus 110 contains noise of a magnetic signal.

Accordingly, the biological information processing section 130 adds such a magnetic signal as to cancel the magnetic signal to be measured as noise, thereby reducing noise.

Although FIG. 10A and FIG. 10B illustrate a case where step S1001 is inserted before step S601 in FIG. 6A and FIG. 6B, step S1001 may be inserted before S601 in FIG. 9A and FIG. 9B.

Thus, by adding a function of reducing noise contained in biological information when the biological information is obtained, it is possible to obtain a better biological information processing result.

Other Embodiments

Although the biological information processing apparatus 120 implements the biological information processing section 130 in the embodiments described above, one or more functions of the biological information processing section 130 may be implemented by the biological information detecting apparatus 110.

The above-described embodiments are illustrative and do not limit the present disclosure. Thus, numerous additional modifications and variations are possible in light of the above teachings. For example, elements and/or features of different illustrative embodiments may be combined with each other and/or substituted for each other within the scope of the present disclosure.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

The invention claimed is:

1. A biological information processing apparatus comprising:
processing circuitry configured to
obtain and store a plurality of pieces of biological information,
set a reference based on a feature amount calculated for each of the pieces of biological information,
discriminate the plurality of pieces of biological information based on the reference that has been set,
determine whether a number of the discriminated pieces of biological information has reached a threshold number, and
perform addition average of the discriminated pieces of biological information after a determination that the number of discriminated pieces of biological information has reached the threshold number;
an input unit configured to receive a correction instruction adjusting the reference; and
a display configured to display a display screen and a correcting screen, the display screen configured to display a biological information processing result obtained by performing the addition average of the pieces of biological information, the correcting screen configured to be used to correct the reference.

2. The biological information processing apparatus according to claim 1,
wherein the reference that has been set is set according to a type of feature amount.

3. The biological information processing apparatus according to claim 1,
wherein the processing circuitry is further configured to correct the reference that has been set, based on the correction instruction received in response to display of the correcting screen.

4. The biological information processing apparatus according to claim 3, wherein the processing circuitry is further configured to:
discriminate the plurality of pieces of biological information based on the adjusted reference, and
perform a corrected addition average of pieces of biological information such that the corrected addition average of pieces of biological information is based on the corrected reference.

5. The biological information processing apparatus according to claim 1,
wherein, the processing circuitry is further configured to calculate a plurality of feature amounts by calculating the feature amount for each of the pieces of biological information, and
the reference is set after a number of the pieces of biological information reaches a threshold number for the obtained plurality of pieces of biological information.

6. A biological information processing system comprising:
a biological information detecting apparatus; and
a biological information processing apparatus, the biological information processing apparatus including processing circuitry configured to to obtain a plurality of pieces of biological information;
set a reference based on a feature amount calculated for each of the pieces of biological information,
discriminate the plurality of pieces of biological information based on the reference that has been set,
determine whether a number of the stored pieces of biological information has reached a threshold number, and
perform addition average of the stored pieces of biological information after a determination that the number of the stored pieces of biological information has reached the threshold number;
an input unit configured to receive a correction instruction; and
a display configured to display a display screen and a correcting screen, the display screen configured to display a biological information processing result obtained by performing the addition average of the pieces of biological information, the correcting screen configured to be used to correct the reference.

7. The biological information processing system of claim 6,
wherein the biological information detection apparatus includes at least one of an electroencephalograph or a biomagnetism measuring apparatus.

8. The biological information processing system of claim 6,
wherein, the processing circuitry is further configured to calculate a plurality of feature amounts by calculating the feature amount for each of the pieces of biological information, and the reference is set after a number of the pieces of biological information reaches a threshold number for the obtained plurality of pieces of biological information.

* * * * *